US009546397B2

(12) United States Patent
Oksenberg et al.

(10) Patent No.: US 9,546,397 B2
(45) Date of Patent: Jan. 17, 2017

(54) SPERM CELL SEPARATION METHODS AND COMPOSITIONS CONTAINING APTAMERS OR NUCLEIC ACID SEQUENCES FOR USE THEREIN

(71) Applicant: Biocern, Inc., Atherton, CA (US)

(72) Inventors: David Oksenberg, Atherton, CA (US); Sergey Krylov, Concord (CA); Michael Musheev, North York (CA)

(73) Assignee: Biocern Inc., Arhterton, CA (US)

( * ) Notice: Subject to any disclaimer, the term of this patent is extended or adjusted under 35 U.S.C. 154(b) by 8 days.

(21) Appl. No.: 14/472,155

(22) Filed: Aug. 28, 2014

(65) Prior Publication Data

US 2015/0203811 A1 Jul. 23, 2015

Related U.S. Application Data

(63) Continuation of application No. 14/149,589, filed on Jan. 7, 2014, now abandoned, which is a continuation of application No. 13/895,603, filed on May 16, 2013, now abandoned, which is a continuation of application No. 13/625,032, filed on Sep. 24, 2012, now abandoned, which is a continuation of application No. 13/369,709, filed on Feb. 9, 2012, now abandoned, which is a continuation of application No. 12/394,993, filed on Feb. 27, 2009, now Pat. No. 8,138,319, which is a continuation-in-part of application No. PCT/US2007/077300, filed on Aug. 30, 2007, application No. 14/472,155, which is a continuation-in-part of application No. 11/817,093, filed on Aug. 24, 2007, now abandoned, which is a continuation-in-part of application No. PCT/US2006/006376, filed on Feb. 24, 2006.

(60) Provisional application No. 60/824,069, filed on Aug. 30, 2006, provisional application No. 60/656,762, filed on Feb. 24, 2005.

(51) Int. Cl.
*C12Q 1/68* (2006.01)
*C12N 5/071* (2010.01)
*C12N 15/115* (2010.01)
*C12N 5/076* (2010.01)

(52) U.S. Cl.
CPC ......... *C12Q 1/6811* (2013.01); *C12N 5/0612* (2013.01); *C12N 15/115* (2013.01); *C12Q 1/6879* (2013.01); *C12N 2310/16* (2013.01); *C12N 2320/10* (2013.01)

(58) Field of Classification Search
None
See application file for complete search history.

(56) References Cited

U.S. PATENT DOCUMENTS

| 4,999,283 | A | 3/1991 | Zavos |
| 5,840,482 | A | 11/1998 | Gray |
| 5,840,504 | A | 11/1998 | Blecher |
| 6,001,988 | A | 12/1999 | Parma |
| 6,126,835 | A | 10/2000 | Barbera-Guillem |
| 8,138,319 | B2 | 3/2012 | Oksenberg |
| 2003/0068654 | A1* | 4/2003 | Benjamin ............ C12N 5/0612 435/7.2 |
| 2004/0142384 | A1 | 7/2004 | Cohen |
| 2005/0003559 | A1* | 1/2005 | Weber ................ G01N 33/5091 436/526 |
| 2005/0114915 | A1* | 5/2005 | Cohen .................. C12N 5/0612 800/21 |
| 2010/0121135 | A1 | 5/2010 | Oksenberg |

FOREIGN PATENT DOCUMENTS

| WO | WO 2006/029258 | 3/2006 |
| WO | WO 2006/078337 | 7/2006 |
| WO | WO 2006/091717 | 8/2006 |
| WO | WO 2008/028081 | 6/2008 |

OTHER PUBLICATIONS

Jayasena, S. Aptamers: an emerging class of molecules that rival antibodies in diagnostics. Clinical Chemistry 45(9):1628-1650 (1999).*
Saito & Inoue. Synthetic biology with RNA motifs. The International Journal of Biochemistry & Cell Biology 41:398-404 (2009).*
Vater et al. Short bioactive Spiegelmers to migraine-associated calcitonin gene-related peptide rapidly indentified by a novel approach: Tailored-SELEX. Nucleic Acids Research 31(21):e130, pp. 1-7 (2003).*
International Search Report issued Mar. 19, 2008 in connection with PCT Appl. No. PCT/US07/77300.

(Continued)

*Primary Examiner* — Samuel Woolwine
(74) *Attorney, Agent, or Firm* — Cooley LLP

(57) ABSTRACT

The present invention provides an aptamer or pool of aptamers (nucleic acid sequences) that bind(s) to a target molecule on the surface, accessible from the surface or inside of a mammalian sperm cell and a method for producing the aptamers. The method comprises contacting a collection of different nucleic acid molecules with the target molecule under conditions favorable for binding between at least one of the nucleic acid molecules and the target molecule, to form at least one complex comprising the nucleic acid molecule bound to the target molecule, wherein each of the nucleic acid molecules comprises at least one segment of randomized nucleotide sequences. The complexes are then separated from the unbound nucleic acid molecules and unbound target molecules, and the bound nucleic acid molecule is recovered from the separated complex. The aptamers are used to separate sperm cells based upon sperm cell qualities, such as whether the cells contain X chromosomes or Y chromosomes.

1 Claim, 3 Drawing Sheets

(56) References Cited

OTHER PUBLICATIONS

Jayasena, "Aptamers: An Emerging Class of Molecules That Rival Antibodies in Diagnostics," Clinical Chemistry, 45(9) 1628-1650, 1999.

Osborne, et al., "Aptamers as Therapeutic and Diagnostic Reagents: Problems and Prospects," Current Opinion in Chemical Biology, 1(1):5-9, 1997.

Supplementary European Search Report, mailed May 31, 2010, in co-pending related EP Application No. EP 07841662, 8 pages.

Saito, et al., "Synthetic biology with RNA motifis," The International Journal of Biochemistry & Cell Biology, 41:398-404, 2009.

Vater, et al., "Short bioactive Spiegelmers to migraine-associated calcitonin gene-related peptide rapidly indentified by a novel approach: Tailored-SELEX," Nucleic Acids Research, 31(2):e130, pp. 1-7, 2003.

\* cited by examiner

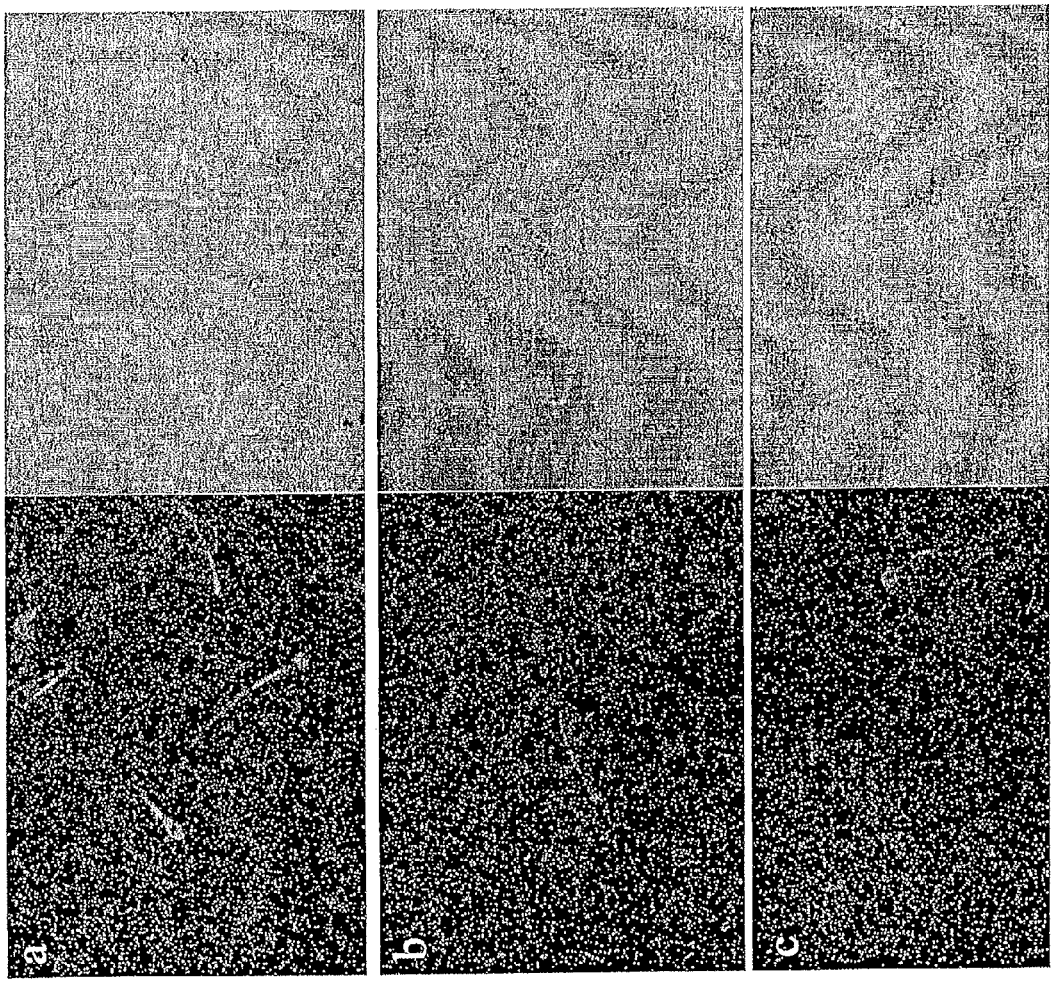
Figure 2A. Binding analysis of the enriched X-cells specific aptamer pool. Fluorescence confocal images of sperm cells (Left), and Optical images of sperm cells (Right). (a) X-specific aptamer pool with the X cells; (b) X-specific aptamer pool with the Y cells; (c) Naïve DNA library with X cells.

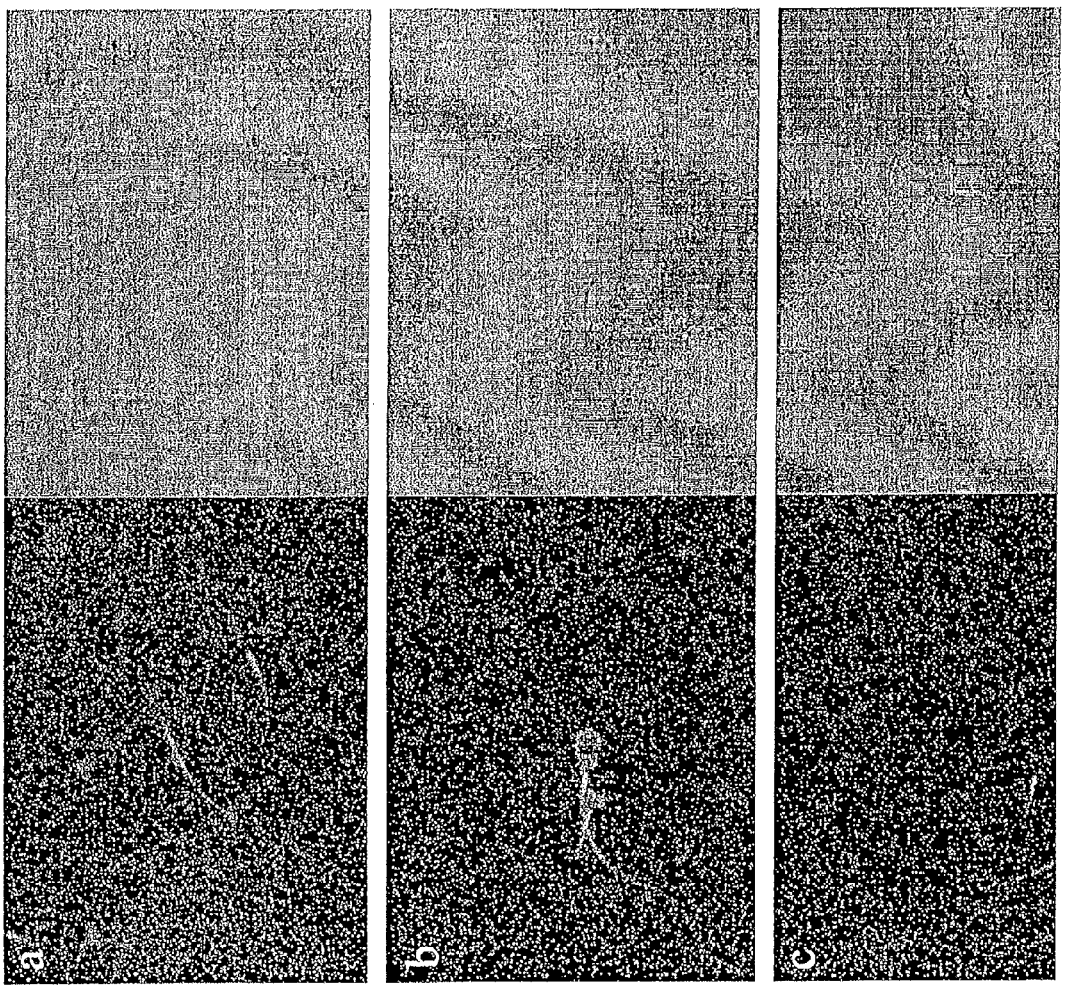
Figure 2B. Binding analysis of the enriched Y-cells specific aptamer pool. Fluorescence confocal images of sperm cells (*Left*), and Optical images of sperm cells (*Right*). (a) Y- specific aptamer pool with the Y cells, (b) Y-specific aptamer pool with the X cells; (c) Naïve DNA library with Y cells.

SEQUENCE LISTING

```
<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(1)
<223> OTHER INFORMATION: May be ALEXA 647 fluorescently labeled

<400> SEQUENCE: 1
ctcctctgac tgtaaccacg                                           20

<210> SEQ ID NO 2
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(1)
<223> OTHER INFORMATION: May be biontiylated

<400> SEQUENCE: 2
ggcttctgga ctacctatgc                                           20

<210> SEQ ID NO 3
<211> LENGTH: 80
<212> TYPE: DNA
<213> ORGANISM: Artificial Sequence
<220> FEATURE:
<223> OTHER INFORMATION: Aptamer

<400> SEQUENCE: 3
ctcctctgac tgtaaccacg caccgaatac agactgtaaa gacagaaagt tcataaacgt     60
gcataggtag tccagaagcc                                           80

<210> SEQ ID NO 4
<211> LENGTH: 80
<212> TYPE: DNA
<213> ORGANISM: Artificial Sequence
<220> FEATURE:
<223> OTHER INFORMATION: Aptamer
```

<400> SEQUENCE: 4
ctcctctgac tgtaaccacg tacgctatta ttattcaata acgataagac ttataatata    60
gcataggtag tccagaagcc                                                80

<210> SEQ ID NO 5
<211> LENGTH: 80
<212> TYPE: DNA
<213> ORGANISM: Artificial Sequence
<220> FEATURE:
<223> OTHER INFORMATION: Aptamer

<400> SEQUENCE: 5
ctcctctgac tgtaaccacg tataatcatc ggggtaagtt gaggcattat ctacgccata    60
gcataggtag tccagaagcc                                                80

<210> SEQ ID NO 6
<211> LENGTH: 81
<212> TYPE: DNA
<213> ORGANISM: Artificial Sequence
<220> FEATURE:
<223> OTHER INFORMATION: Aptamer

<400> SEQUENCE: 6
ctcctctgac tgtaaccacg ataccaatac gtaaattcta taaggcatac atattataca    60
agcataggta gtccagaagc c                                              81

<210> SEQ ID NO 7
<211> LENGTH: 80
<212> TYPE: DNA
<213> ORGANISM: Artificial Sequence
<220> FEATURE:
<223> OTHER INFORMATION: Aptamer

<400> SEQUENCE: 7
ctcctctgac tgtaaccacg tctggaacat gatgcaggtg tctaacagta tgaatacttg    60
gcataggtag tccagaagcc                                                80

<210> SEQ ID NO 8
<211> LENGTH: 80
<212> TYPE: DNA
<213> ORGANISM: Artificial Sequence
<220> FEATURE:
<223> OTHER INFORMATION: Aptamer

<400> SEQUENCE: 8
ctcctctgac tgtaaccacg ctgtcgacta cagatcacta ctttcgctaa ggtacctcaa    60
gcataggtag tccagaagcc                                                80

<210> SEQ ID NO 9
<211> LENGTH: 80
<212> TYPE: DNA
<213> ORGANISM: Artificial Sequence
<220> FEATURE:
<223> OTHER INFORMATION: Aptamer

<400> SEQUENCE: 9
ctcctctgac tgtaaccacg pataacgttt ttcatctatt tgtttactta atacctaata    60
gcataggtag tccagaagcc                                                80

<210> SEQ ID NO 10

```
<211> LENGTH: 80
<212> TYPE: DNA
<213> ORGANISM: Artificial Sequence
<220> FEATURE:
<223> OTHER INFORMATION: Aptamer

<400> SEQUENCE: 10
ctcctctgac tgtaaccacg attgtattag ttaacgatac ttattatttg taagttatta    60
gcataggtag tccagaagcc                                                80

<210> SEQ ID NO 11
<211> LENGTH: 63
<212> TYPE: DNA
<213> ORGANISM: Artificial Sequence
<220> FEATURE:
<223> OTHER INFORMATION: Aptamer

<400> SEQUENCE: 11
ctcctctgac tgtaaccacg aataacatta catatagtta cttgcatagg tagtccagaa    60
gcc                                                                  63

<210> SEQ ID NO 12
<211> LENGTH: 80
<212> TYPE: DNA
<213> ORGANISM: Artificial Sequence
<220> FEATURE:
<223> OTHER INFORMATION: Aptamer

<400> SEQUENCE: 12
ctcctctgac tgtaaccacg gtaaacatga taataatact tctccttttg taatggattt    60
gcataggtag tccagaagcc                                                80

<210> SEQ ID NO 13
<211> LENGTH: 80
<212> TYPE: DNA
<213> ORGANISM: Artificial Sequence
<220> FEATURE:
<223> OTHER INFORMATION: Aptamer

<400> SEQUENCE: 13
ctcctctgac tgtaaccacg ggtacatata tccctattaa ttgacacata tatttactta    60
gcataggtag tccagaagcc                                                80

<210> SEQ ID NO 14
<211> LENGTH: 80
<212> TYPE: DNA
<213> ORGANISM: Artificial Sequence
<220> FEATURE:
<223> OTHER INFORMATION: Aptamer

<400> SEQUENCE: 14
ctcctctgac tgtaaccacg catcatttcg ctaatagata aagtgttcgt cgtcagagca    60
gcataggtag tccagaagcc                                                80

<210> SEQ ID NO 15
<211> LENGTH: 80
<212> TYPE: DNA
<213> ORGANISM: Artificial Sequence
<220> FEATURE:
<223> OTHER INFORMATION: Aptamer

<400> SEQUENCE: 15
ctcctctgac tgtaaccacg atacatttac gtaaattcta ttaacattta tattctacat    60
```

```
gcataggtag tccagaagcc                                                        80

<210> SEQ ID NO 16
<211> LENGTH: 80
<212> TYPE: DNA
<213> ORGANISM: Artificial Sequence
<220> FEATURE:
<223> OTHER INFORMATION: Aptamer

<400> SEQUENCE: 16
ctcctctgac tgtaaccacg taatattaac tttaaactcc aatactgtta tttatcaagt           60
gcataggtag tccagaagcc                                                        80

<210> SEQ ID NO 17
<211> LENGTH: 80
<212> TYPE: DNA
<213> ORGANISM: Artificial Sequence
<220> FEATURE:
<223> OTHER INFORMATION: Aptamer

<400> SEQUENCE: 17
ctcctctgac tgtaaccacg gtatatcgac ttattacaat gataagtatt attaaactta           60
gcataggtag tccagaagcc                                                        80

<210> SEQ ID NO 18
<211> LENGTH: 80
<212> TYPE: DNA
<213> ORGANISM: Artificial Sequence
<220> FEATURE:
<223> OTHER INFORMATION: Aptamer

<400> SEQUENCE: 18
ctcctctgac tgtaaccacg aaacattaca tggaacttga tcgtttagga taataaatgc           60
gcataggtag tccagaagcc                                                        80

<210> SEQ ID NO 19
<211> LENGTH: 80
<212> TYPE: DNA
<213> ORGANISM: Artificial Sequence
<220> FEATURE:
<223> OTHER INFORMATION: Aptamer

<400> SEQUENCE: 19
ctcctctgac tgtaaccacg tgtaccactt tctgttacgc taatggcaca ctacacttaa           60
gcataggtag tccagaagcc                                                        80

<210> SEQ ID NO 20
<211> LENGTH: 70
<212> TYPE: DNA
<213> ORGANISM: Artificial Sequence
<220> FEATURE:
<223> OTHER INFORMATION: Aptamer

<400> SEQUENCE: 20
ctcctctgac tgtaaccacg taacttggaa taatacttct tgtaaatttt gcataggtag           60
tccagaagcc                                                                   70

<210> SEQ ID NO 21
<211> LENGTH: 80
<212> TYPE: DNA
<213> ORGANISM: Artificial Sequence
<220> FEATURE:
```

-continued

<223> OTHER INFORMATION: Aptamer

<400> SEQUENCE: 21
ctcctctgac tgtaaccacg taaatatatg agttatttat gagttcattg aattctactt    60
gcataggtag tccagaagcc    80

<210> SEQ ID NO 22
<211> LENGTH: 80
<212> TYPE: DNA
<213> ORGANISM: Artificial Sequence
<220> FEATURE:
<223> OTHER INFORMATION: Aptamer

<400> SEQUENCE: 22
ctcctctgac tgtaaccacg gagtcagcct gatctacctt caaaggccac taggccttga    60
gcataggtag tccagaagcc    80

<210> SEQ ID NO 23
<211> LENGTH: 80
<212> TYPE: DNA
<213> ORGANISM: Artificial Sequence
<220> FEATURE:
<223> OTHER INFORMATION: Aptamer

<400> SEQUENCE: 23
ctcctctgac tgtaaccacg tatacttact ttactaaaac tactactaag taagtaaaca    60
gcataggtag tccagaagcc    80

<210> SEQ ID NO 24
<211> LENGTH: 80
<212> TYPE: DNA
<213> ORGANISM: Artificial Sequence
<220> FEATURE:
<223> OTHER INFORMATION: Aptamer

<400> SEQUENCE: 24
ctcctctgac tgtaaccacg tatcacttac atttaaatca atgtatatca atattttagt    60
gcataggtag tccagaagcc    80

<210> SEQ ID NO 25
<211> LENGTH: 80
<212> TYPE: DNA
<213> ORGANISM: Artificial Sequence
<220> FEATURE:
<223> OTHER INFORMATION: Aptamer

<400> SEQUENCE: 25
ctcctctgac tgtaaccacg tcaggataat gatcataaga tatctttatg tatatactat    60
gcataggtag tccagaagcc    80

<210> SEQ ID NO 26
<211> LENGTH: 80
<212> TYPE: DNA
<213> ORGANISM: Artificial Sequence
<220> FEATURE:
<223> OTHER INFORMATION: Aptamer

<400> SEQUENCE: 26
ctcctctgac tgtaaccacg ccagttcgtc atcagattcc atctttagct acttacaact    60
gcataggtag tccagaagcc    80

```
<210> SEQ ID NO 27
<211> LENGTH: 80
<212> TYPE: DNA
<213> ORGANISM: Artificial Sequence
<220> FEATURE:
<223> OTHER INFORMATION: Aptamer

<400> SEQUENCE: 27
ctcctctgac tgtaaccacg caaaagtcac tggccgttcg agttatatga gtagggagag    60
gcataggtag tccagaagcc                                                80

<210> SEQ ID NO 28
<211> LENGTH: 80
<212> TYPE: DNA
<213> ORGANISM: Artificial Sequence
<220> FEATURE:
<223> OTHER INFORMATION: Aptamer

<400> SEQUENCE: 28
ctcctctgac tgtaaccacg ccagaccgga tccctgatgt atttattttc ggaaggttga    60
gcataggtag tccagaagcc                                                80

<210> SEQ ID NO 29
<211> LENGTH: 80
<212> TYPE: DNA
<213> ORGANISM: Artificial Sequence
<220> FEATURE:
<223> OTHER INFORMATION: Aptamer

<400> SEQUENCE: 29
ctcctctgac tgtaaccacg taatgagtga cgaaagtgtc agatggagcc ttctacctgt    60
gcataggtag tccagaagcc                                                80

<210> SEQ ID NO 30
<211> LENGTH: 80
<212> TYPE: DNA
<213> ORGANISM: Artificial Sequence
<220> FEATURE:
<223> OTHER INFORMATION: Aptamer

<400> SEQUENCE: 30
ctcctctgac tgtaaccacg cgattaaaac cggcagttat ctcttagcaa gcctgatcct    60
gcataggtag tccagaagcc                                                80

<210> SEQ ID NO 31
<211> LENGTH: 81
<212> TYPE: DNA
<213> ORGANISM: Artificial Sequence
<220> FEATURE:
<223> OTHER INFORMATION: Aptamer

<400> SEQUENCE: 31
ctcctctgac tgtaaccacg ggttcaatgt aagggttggt gtggttggac tagcgctcag    60
tgcataggta gtccagaagc c                                              81

<210> SEQ ID NO 32
<211> LENGTH: 80
<212> TYPE: DNA
<213> ORGANISM: Artificial Sequence
<220> FEATURE:
<223> OTHER INFORMATION: Aptamer

<400> SEQUENCE: 32
```

```
ctcctctgac tgtaaccacg gcatatgtga gcatcgaata gctggcgacg aaccagattc      60
gcataggtag tccagaagcc                                                  80

<210> SEQ ID NO 33
<211> LENGTH: 80
<212> TYPE: DNA
<213> ORGANISM: Artificial Sequence
<220> FEATURE:
<223> OTHER INFORMATION: Aptamer

<400> SEQUENCE: 33
ctcctctgac tgtaaccacg acgacagtca tccctgactc ggatcttaca tgtcgttaca      60
gcataggtag tccagaagcc                                                  80

<210> SEQ ID NO 34
<211> LENGTH: 80
<212> TYPE: DNA
<213> ORGANISM: Artificial Sequence
<220> FEATURE:
<223> OTHER INFORMATION: Aptamer

<400> SEQUENCE: 34
ctcctctgac tgtaaccacg ttaaatctta taggattcta gtgtacaaat atataactta      60
gcataggtag tccagaagcc                                                  80

<210> SEQ ID NO 35
<211> LENGTH: 80
<212> TYPE: DNA
<213> ORGANISM: Artificial Sequence
<220> FEATURE:
<223> OTHER INFORMATION: Aptamer

<400> SEQUENCE: 35
ctcctctgac tgtaaccacg caaaagtcac tggccgttcg agttatatga gtagggagag      60
gcataggtag tccagaagat                                                  80
```

SPERM CELL SEPARATION METHODS AND COMPOSITIONS CONTAINING APTAMERS OR NUCLEIC ACID SEQUENCES FOR USE THEREIN

RELATED APPLICATIONS

This application is a continuation of U.S. Ser. No. 14/149,589, filed Jan. 7, 2014, which is a continuation of U.S. Ser. No. 13/895,603, filed May 16, 2013, which is a continuation of U.S. Ser. No. 13/625,032, filed Sep. 24, 2012, which is a continuation of U.S. Ser. No. 13/369,709, filed Feb. 9, 2012, which is a continuation of U.S. Ser. No. 12/394,993, filed Feb. 27, 2009, now U.S. Pat. No. 8,138,319, which is a continuation-in-part (CIP) of PCT/US2007/077300 filed on Aug. 30, 2007, which claims priority to U.S. Provisional Patent Application No. 60/824,069, filed Aug. 30, 2006, and this application is also a continuation-in-part (CIP) of U.S. Ser. No. 11/817,091, filed on Aug. 24, 2007, which claims priority to PCT/US2006/006376 filed on Feb. 24, 2006, which claims priority to U.S. Provisional Patent Application No. 60/656,762, filed Feb. 24, 2005, all of which are herein incorporated by reference in their entirety.

DESCRIPTION OF THE TEXT FILE SUBMITTED ELECTRONICALLY

The contents of the text file submitted electronically herewith are incorporated, herein by reference in their entirety: A computer readable format copy of the Sequence Listing (filename: BICE_003_04US_SeqList.txt, date recorded: Sep. 24, 2012, file size 10 kilobytes).

FIELD OF THE INVENTION

The present invention relates to methods and compositions for identifying and separating cells from a population of cells, particularly, mammalian sperm cells through the use of nucleic acids, particularly aptamers, that specifically bind with high affinity and specificity or preferentially to either sperm cells containing the X chromosome or the Y chromosome.

BACKGROUND OF THE INVENTION

The ability to select sperm cells having desired characteristics remains an important objective in artificial reproduction. An efficient and cost effective process for identifying and separating sperm cells for sex selection would have significant economic implications for the livestock industry and in particular in the beef and dairy industry. For instance, in the beef industry, male bulls have greater commercial value than female cattle because of their size, so methods that allow for enrichment of male bulls would provide a clear competitive advantage to ranchers who use such techniques. On the other hand, in the dairy industry, milk-producing cows are generally more desirable. Currently however, only a small percentage of cattle ranchers employ artificial insemination methods involving sex-specific sperm cells as a means to produce livestock having the desired sex. Despite the advantages of being able to control and plan the sexual makeup of en inventory of cattle, such an approach is not more widely used in the industry because current methods for sorting sperm cells into sex-specific sperm cells, which employ flow cytometry techniques, are both expensive and involve irreversible staining of the sperm cells prior to insemination. Less costly and intrusive methods for identifying and separating sperm cells based on sperm cell quality, physical characteristics, or content would also have important applications in many animal and human reproductive technologies.

SUMMARY OF THE INVENTION

The present invention provides at least one aptamer or nucleic acid sequence that binds to a target molecule accessible from the surface of a cell, particularly, a mammalian sperm cell and a method for producing the aptamers or nucleic acid sequence. The method comprises contacting a collection of different nucleic acid molecules with the target molecule under conditions favorable for binding between at least one of the nucleic acid molecules and the target molecule, to form at least one complex comprising the nucleic acid molecule bound to the target molecule, wherein each of the nucleic acid molecules comprises at least one segment of randomized nucleotide sequences. The complexes are then separated from the unbound nucleic acid molecules and unbound target molecules, and the bound nucleic acid molecule is recovered from the separated complex.

The present invention further provides one or more specific nucleic acid molecules or aptamers, preferably an oligonucleotide, more preferably a DNA molecule, that binds preferentially to either a sperm cell containing a X-chromosome (hereinafter referred to as a "X sperm cell") or a sperm cell containing a Y-chromosome (hereinafter referred to as a "Y sperm cell"), and preferably preferentially binds better to one of the X sperm cells or binds with significantly different affinities to each type of X and Y sperm cells.

The present invention also provides an isolated non-naturally occurring nucleic acid sequence or aptamer that binds to a target molecule on, accessible from the surface or inside of a mammalian sperm cell comprising a nucleotide sequence selected from the group consisting of: a nucleotide sequence selected from the group consisting of SEQ ID NOS: 3-35 or a target molecule binding portion thereof.

The present invention also provides a method for using the aptamers or nucleic acid sequence to identify, select and separate X and Y sperm cells. Preferably, the method comprises separating the mammalian sperm cells by contacting the X and Y sperm cells with at least one aptamer of the invention and separating the cells into two or more populations based upon their ability to preferentially bind to the aptamer.

The invention further includes the X and Y sperm cell population(s) produced by the separation method. The invention further comprises an artificial insemination kit comprising the sperm cell population produced by the method of the invention, and a method for artificial insemination of a mammal by administering the selected sperm cell population to the mammal.

The present invention also provides diagnostic and technological means relating to sperm cell qualities such as sperm cell viability, motility, functionality, stimulation, and preservation, as well as diagnostic and technological means that address insemination rates, fertilization rates, and birth rates of desirable offspring, by establishing a method of selectively sorting semen or sperm cells obtained from various species, individuals, and specimens.

DETAILED DESCRIPTION OF THE FIGURES

FIG. 1 is a flow cytometry graph showing the specificity of DNA aptamer pools to live sorted bull spermatozoa after 9 aptamer selection rounds (A=Y sorted bull semen cells binding to a naïve DNA library; B=Y sorted bull semen cells binding to the X cell specific aptamer pool; C=X sorted bull semen cells binding to a naïve DNA library; and D=X sorted bull semen cells binding to the X cell specific aptamer pool).

FIG. 2A shows the binding analysis of the enriched X-cells specific aptamer pool. Fluorescence confocal images of sperm cells (Left); and optical images of sperm cells (Right). (a) X-specific aptamer pool with the X cells, (b) X-specific aptamer pool with the Y cells; (c) Naïve DNA library with X cells.

FIG. 2B shows the binding analysis of the enriched Y-cells specific aptamer pool. Fluorescence confocal images of sperm cells (Left); and Optical images of sperm cells (Right). (a) Y-specific aptamer pool with the Y cells, (b) Y-specific aptamer pool with the X cells; (c) Naïve DNA library with Y cells.

DETAILED DESCRIPTION OF THE INVENTION

Figure 1:
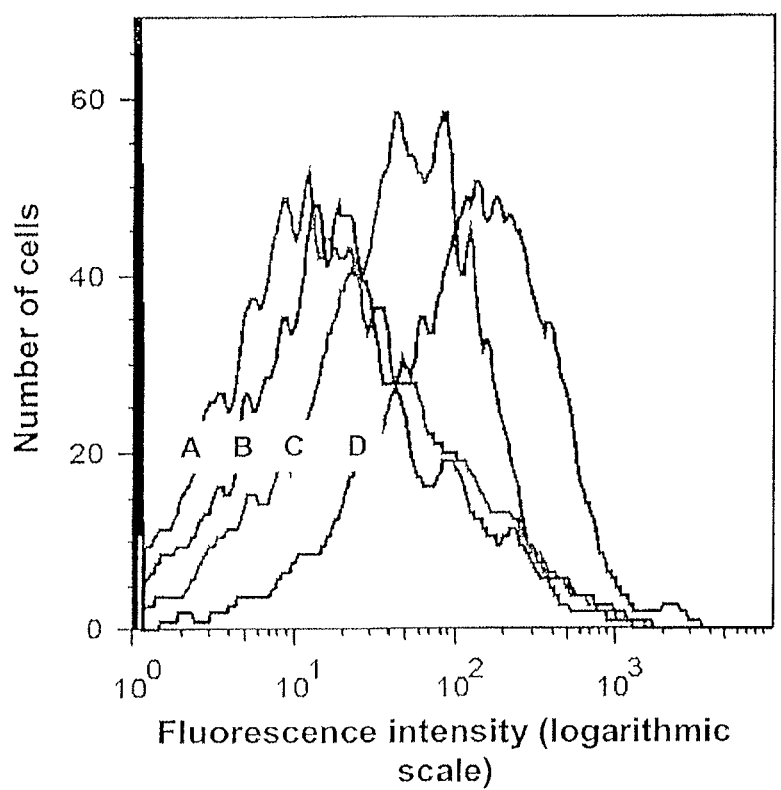

Within the context of the present invention, aptamers are defined as a class of ligands or nucleic acid sequences, the terms of which are used interchangeably throughout this specification; also are referred to a oligomers or oligonucleotides, i.e., nucleic acids that bind preferentially to a particular target molecule, such as a polypeptide, a short peptide, an enzyme, a protein, a lipid, a glycolipid, a phospholipid, a glycoprotein, a carbohydrate, a small molecule or a cell surface molecule, such as a receptor, an extracellular matrix or scaffolding molecule or an ion channel. The aptamers of the present invention are ligands or single-stranded oligonucleotides that bind with high affinity and specificity to target molecules through complementary shape interactions. The aptamers or nucleic acid sequences of the present invention are capable of binding or forming a complex with a target molecule to a higher degree or affinity than the aptamer would bind to contaminating or control molecules that presumably do not contain the target on the surface of or accessible from the surface of a X or Y sperm cells. The aptamers or nucleic acid sequences of the present invention may bind preferentially to a target molecule on the surface of the X sperm cell as compared to the Y sperm cell or vice versa. The target molecule also may be accessible from the surface of the X or Y sperm cell, and therefore, the target molecule may be contained inside the X or Y sperm cell. An aptamer within the meaning of the present invention will preferentially bind to a target molecule in or on the X sperm cell as compared the Y sperm cell. Thus, useful aptamers of the present invention can distinguish between X and Y sperm cells and can preferentially bind to target molecules in one of these types of sperm cells as compared to the other type. For example, the X chromosome in the X sperm cell provides a target molecule that is not contained in the Y sperm cell, and vice versa, the Y chromosome in the Y sperm cell provides a target molecule that is not contained in the X sperm cell. The aptamers of the present invention may bind preferentially to the X chromosome, for example, the chromatin, which is the complex combination of DNA, RNA and proteins (histones and nonhistones), of which the chromosome is composed as compared to the Y chromosome, also composed of the complex of DNA, RNA and proteins. The nucleic acids of the aptamers may be either DNA, RNA, single-stranded or double-stranded, and any chemical modifications thereof. Modifications include, but are not limited to, those that provide other chemical groups that incorporate additional charge, polarizability, hydrogen bonding, electrostatic interaction, fluxionality or a label to the nucleic acid bases or to the nucleic acid molecule as a whole. Preferably, the aptamers are DNA molecules. Most preferably, they are oligonucleotides.

The length of these molecules is inure than one nucleotide and may include short sequences, such as dimers or trimers, that may be intermediates in the production of specific nucleic acid molecules that bind to a target. Aptamers of the present invention include nucleic acid molecules of any length but preferably less than 200 nucleotides, preferably less than 150 nucleotides, preferably less than 100 nucleotides, preferably less than 80 nucleotides, more preferably less than 60 nucleotides, more preferably less than 40 nucleotides, preferably less than 35 nucleotides, preferably less than 30 nucleotides, preferably less than 25 nucleotides, preferably less than 20 nucleotides, preferably less than 15 nucleotides and preferably less than 10 nucleotides. Typically, such oligonucleotides are about 15-60 nucleotides long.

Within the context of the present invention, aptamers are understood to include both monoclonal aptamers and polyclonal aptamers. As used herein, monoclonal aptamers are ones with the same nucleotide sequences that bind to the same target, and polyclonal aptamers are ones with some variation in nucleotide sequences, which bind to the same target. Monoclonal aptamers are preferred. As used herein, an aptamer, preferably is an oligonucleotide that is capable of complexing or binding to a target molecule as described herein. The affinity or complexation of an aptamer to its target molecule is a matter of degree and is measured by the ability of the aptamer to bind to the target molecule at a higher degree than to a control or contaminating molecules. Thus, specificity of aptamers is similar in meaning to the specificity as it applies to antibodies.

Once useful aptamers that bind preferentially to either of the X sperm cells or the Y sperm cells are identified by one of the methods disclosed herein, the aptamers can be prepared by any known method of producing nucleic acid molecules, such as synthetic, recombinant and purification methods. Additionally, the aptamers may be linked to another molecule to assist with the detection and/or isolation after contacting the aptamer to the sperm cell. It is important that this additional molecule would not significantly affect or interfere with the binding affinity of the aptamer to the target molecule. Useful labels would include labels known to be useful for isolation and detection of proteins, peptides, metabolites and antibodies, such as fluorescent or biotin moieties or magnetic beads or other types of beads useful for isolation.

Aptamers or nucleic acid sequences of the present invention can be used alone or in combination with other aptamers specific for the same target molecule. Different aptamers that contain the same consensus would be known from the comparison of two or more known aptamers to a specific target molecule or possibly another target molecule on, in or near the surface of an X or Y sperm cell. If X and Y sperm cells are to be separated, it is important to employ one or more aptamers specific or preferential for one cell or the other to provide the best separation to obtain a sperm population of either X containing or Y containing sperm cells.

Aptamers for sperm cell surface proteins or other sperm cell surface targets (including, but not limited to, carbohydrates, lipids, nucleotides and other small molecules that may be accessible to bind to specific aptamers) are identified and selected by the methods of the invention. In one embodiment, the invention provides a method for producing an aptamer that binds to a target molecule on the surface of a mammalian sperm cell. A collection of different nucleic acid molecules is contacted with a target molecule that is accessible for binding to these molecules, likely on the cell surface or protruding from the cell surface, accessible from the cell surface, or inside the cell. under conditions favorable for binding between at least one of the nucleic acid molecules and the target molecule. Each of the nucleic acid molecules contains at least one segment of randomized nucleotide sequences. This provides variation in the nucleic acid molecules. The contact results in the formation of at least one complex comprising at least one nucleic acid molecule bound to the target molecule. The complexes are then separated from the unbound nucleic acid molecules and the unbound target molecules. Then, the bound nucleic acid molecule is recovered from the separated complex, thus providing the desired aptamer. In a further embodiment, the method comprises the further step of amplifying the recovered nucleic acid molecules to create additional molecules. In a further, preferred embodiment, the recovered and amplified molecules, i.e., aptamers, are further mixed with the collection of X and Y sperm cells containing target molecules accessible for binding, preferably on or accessible from the cell surface or in the cell, and the sequence of steps stated above is repeated a sufficient number of times until aptamers of a desired specificity/preferentially and binding affinity are recovered. The aptamers bind more specifically with a target molecule on a cell as compared to a control pool of DNA sequences to the same cell. In an alternative embodiment, the contacting step comprises incubating the molecules to form an equilibrium mixture and the separating step comprises capillary electrophoresis.

Preferably, the target molecule on the surface of a cell is one that is unique to either a X sperm cell or a Y sperm cell and that will not cross react with each type of cell. Such a target molecule, can be a protein, a peptide, an enzyme, a lipid, a glycolipid, a phospholipid, a glycoprotein, a carbohydrate, a small molecule or a cell surface molecule, such as a receptor, an extracellular matrix or scaffolding molecule or an ion channel. Most preferably, the protein distinguishes X sperm cells from Y sperm cells containing a Y chromosome. But the target molecule can be present inside of or accessible from the surface of the cell, and therefore not be present on the cell surface. Because the aptamers of the present invention distinguish between X and Y chromosome containing sperm cells, the aptamers may differentially bind to the X and Y chromosomes of these cells or target molecules that are encoded by the X and Y chromosomes.

In one embodiment of the invention, the methods of the invention are performed in an iterative fashion such that there are repeated steps of (a) contacting a collection of different nucleic acids (i.e., aptamers) with a target molecule accessible from the surface of a cell to form at least one complex comprising at least one nucleic acid molecule bound to a target molecule accessible from the surface of a cell, (h) separating the complexes from unbound nucleic acid molecules and unbound target molecules; and (c) recovering the bound nucleic acid molecule from the separated complex. In this embodiment, a plurality of aptamers recovered from the separated complex of step (e) are used in a subsequent round of the method in step (a). In one embodiment of the invention, the steps of the sorting sperm cells (i.e., steps (a), (b) and (c) above) are repeated 1 or more, 2 or more, 3 or more, 4 or more, 5 or more, 6 or more, 7 or more, 8 or more, 9 or more, 10 or more, or 11 or more times to produce an aptamer pool specific for X sperm culls or Y sperm cells. Sorted aptamers can be purified by methods known in the art and sequenced by known methods or a commercial vendor.

Representative aptamers produced by the method disclosed herein comprise an isolated non-naturally occurring nucleic acid sequence that binds to a target molecule on a mammalian sperm cell comprising as nucleotide sequence selected from the group consisting of:

(a) a nucleotide sequence selected from the group consisting of SEQ ID NOS: 3-35 or a target molecule binding portion thereof;

(b) a nucleotide sequence which is substantially homologous to and has substantially the same ability to bind said target molecule on said sperm cell as the nucleotide sequence of (a) or a target molecule binding portion thereof; and (c) a nucleotide sequence having substantially the same structure and has substantially the same ability to bind said target molecule on said sperm cell as the nucleotide sequence of (a) or (b) or a target molecule binding portion thereof.

The isolated non-naturally occurring nucleic acid sequence as described above also encompasses at least a portion of nucleotides 1-20 are deleted from said SEQ ID NOS: 3-35 or a target molecule binding portion thereof; at least a portion of nucleotides 61-80 are deleted from said SEQ ID NOS: 3-10 and 12-35 or nucleotides 44-63 of SEQ ID NO: 11 or a target molecule binding portion thereof; at least a portion of nucleotides 1-20 are deleted from said SEQ ID NOS: 3-35 and/or wherein at least a portion of nucleotides 61-80 are deleted from said SEQ ID NOS: 3-10 or 12-35 or nucleotides 44-63 of SEQ ID NO: 11 or a target molecule binding portion thereof; and DNA sequences comprises nucleotides 21-60 of SEQ ID NOS: 3-10 or 12-35 or nucleotides 21-43 of SEQ 11) NO: 11 or a target molecule binding portion thereof.

The present invention also encompasses a composition comprising at least one of the nucleic acid sequences selected from the group consisting of all of the nucleic acid sequences enumerated in [0020] and [0021] above.

The present method further comprises the step of amplifying the recovered nucleic acid molecule to create additional nucleic acid molecules. The contacting step (a) may comprise incubating the molecules to form an equilibrium mixture and wherein the separating step comprises capillary electrophoresis.

The present method further comprises incubating the collection of different nucleic acid molecules or aptamers after each round and sperm cells containing the target molecule with a primer that is substantially complementary to template nucleic acid sequence. The template nucleic acid sequence is a sequence that corresponds to a segment of the aptamer that is unvaried (or constant) within a plurality of aptamers. The aptamer preferably is from a DNA library and this template nucleic acid sequence is a vector sequence. The contacting step (a) further comprises a negative selection step followed by a positive selection step. The plurality of the recovered aptamers are quantified using the know technique of flow cytometry.

The target molecule on the sperm cell to which the aptamer can bind is selected from the group consisting of a protein, a peptide, an enzyme, a lipid, a glycolipid, a phospholipid, a glycoprotein, a carbohydrate, a small molecule or a cell surface molecule. In a preferred embodiment the target molecule is a target molecule contained on a sperm cell and the target molecule distinguishes at least one X sperm cell from at least one Y sperm cell by a comparison of the binding or no binding or differential binding. The sperm cells identified by this method are cattle sperm cells or human sperm cells.

Aptamers that specifically bind to sperms cells can be identified by methods known in the art, including, but not limited to cell sorting and flow cytometry techniques. The present method provides a method of preparing aptamers that permits separation of mammalian X sperm cells from mammalian Y sperm cells, wherein the method produces a first group of aptamers that bind to X sperm cells in the first sample and a second group of aptamers that bind to Y sperm cells in the second sample; and the method further comprises: (d) comparing the first and second groups of aptamers to identify by process elimination at least one aptamer that binds only to either the X sperm cells or the Y sperm cells. The first and second samples of mammalian sperm cells are produced by flow cytometry and cell sorting.

The method of preparing sperm specific aptamers further comprises a contacting step (a) which further comprises: (a1) contacting a first collection of different nucleic acid molecules with a target molecule contained in a first sample of mammalian X sperm Cells under conditions favorable for binding between the nucleic acid molecules and the X sperm cells to form at least one complex comprising at least one nucleic acid molecule bound to at least one X sperm cell, wherein each of the nucleic acid molecules comprises at least one segment of randomized nucleotide sequences; and (a2) contacting a second collection of different nucleic acid molecules with a target molecule contained in a second sample of mammalian Y sperm cells under conditions favorable for binding between the nucleic acid molecules and the Y sperm cells to form at least one complex comprising at least one nucleic acid molecules bound to at least one Y sperm cell, wherein each of the nucleic acid molecules comprises at least one segment of randomized nucleotide sequences; wherein the separation step (b) and the recovery step (c) thereby produces aptamers for X sperm cells and aptamers for Y sperm cells. The aptamers recovered by this method are those that bind to X sperm cells and those that bind to Y sperm cells.

The method of producing sperm specific aptamers further comprises that prior to step (a), at least 1 round of contact of the nucleic acid molecules with an unsorted cell population comprising both mammalian X sperm cells and Y sperm cells occurs. Also the separating step (b) further comprises the step of separating the sperm cells bound to the aptamer from the aptamer and the recovering step (c) further comprises recovering the separated sperm cells. The mammalian sperm cells preferably are cattle sperm cells or human sperm cells.

In one embodiment of the invention, rounds of unsorted aptamer selection can be performed prior to rounds of sorted X and Y sperm cell/aptamer selection. For instance, 1 to 5 rounds of unsorted aptamer selection can be performed. The invention includes methods comprising 3 rounds of unsorted aptamer selection prior to rounds of sorted aptamer selection. The method of claim 1, further comprises incubating the collection of different nucleic acid molecules and the target molecule with a primer that is substantially complementary to template nucleic acid sequence.

In an alternative and preferred embodiment, the invention provides a method for producing an aptamer that permits separation of X sperm cells from Y sperm cells. A first sample of X sperm cells is obtained, and a second sample of Y sperm cells is obtained. A first group of aptamers are produced, which bind to the X sperm cells in the first sample, and a second group of aptamers are produced that bind to the Y sperm cells in the second sample. The first and second groups of aptamers are compared to identify by a process of elimination at least one aptamer that binds to either of the X sperm cells or the Y sperm cells. Generally, several different aptamers are identified that bind to either type of cells.

Preferably, the first and second samples of mammalian sperm cells, which contain either Y sperm cells or X sperm cells are produced by flow cytometry and cell sorting techniques that are known to those skilled in the art. Such techniques are disclosed in U.S. Pat. No. 5,135,759, issued Aug. 4, 1992. Generally, a flow cytometer measures the amount of fluorescent light given off when the sperm, previously treated with a fluorescent dye, passes through a laser beam. The dye hinds to the DNA. Because the X chromosome contains more DNA than the Y chromosome, the female (X) sperm takes up more dye and gives off more fluorescent light than the male (Y) sperm. To detect the small differences in DNA between the X and the Y sperm, the sperm passes single file through the laser beam, which measures the DNA content of individual sperm. This permits separation of the individual X and Y sperm cells by a cell sorter. Sorted X and Y sperm cells can be purchased from commercial sources which have been sorted using similar cell sorting methods.

Preferably, the aptamers are produced by a process comprising the steps of: (a) contacting a first collection of different nucleic acid molecules with a first sample of Y sperm cells under conditions favorable for binding between the nucleic acid molecules and the Y sperm cells to form at least one complex comprising at least one nucleic acid molecules bound to at least one Y chromosome-bearing sperm cell, wherein each of the nucleic acid molecules comprises at least one segment of randomized nucleotide sequences; (b) contacting a second collection of different nucleic acid molecules with the second sample of X sperm cells under conditions favorable for binding between the nucleic acid molecules and the X sperm cells to form at least one complex comprising at least one nucleic acid molecule bound to at least one X sperm cell, wherein each of the nucleic acid molecules comprises at least one segment of randomized nucleotide sequences; (c) separating the complexes from the unbound nucleic acid molecules and unbound target molecules; and (d) recovering the bound nucleic acid molecules from the complexes, thereby producing aptamers for Y sperm cells and aptamers for X sperm cells.

In a preferred embodiment, the aptamers are tested and validated by contacting them with a sample of sperm cells containing X sperm cells and Y sperm cells, separating the sperm cells by flow cytometry and cell sorting, and determining that the putative X-binding aptamer binds to the X sperm cell and the putative Y-binding aptamer binds to the Y sperm cell. Generally, the aptamers are labeled, for example, with a fluorescent moiety to permit the appropriate identification.

In producing the aptamers of the invention various specific techniques known to those skilled in the art may be used. One such technique is the MonoLex process of AptaRes, Luckenwalde, Germany. The process involves the steps of: (1) synthesis of an oligonucleotide library with regions of random sequence; (2) affinity adsorption of the oligonucleotides to a target; (3) affinity sorting of the oligonucleotides along an affinity resin; (4) separation of the oligonucleotides with different levels of affinity into numerous pools comprising multiple aptamers per pool; (5) amplification of the separated nucleotide pools (which produces polyclonal aptamers); and (6) identification of individual oligonucleotides by cloning and sequencing (which produces monoclonal aptamers).

Another technique is known as the SELEX (Systematic Evolution of Ligands by EXponential enrichment) process. The SELEX process and variants thereof are described in U.S. Pat. Nos. 5,861,254; 6,261,774 B1; 6,376,190 B1; 6,506,887 B1; 6,706,482 B2 and 6,730,482 B2. This process includes the steps of: (1) contacting a mixture of nucleic acids, preferably comprising segments of randomized sequences, with a target under conditions favorable for binding; (2) partitioning unbound nucleic acids from those nucleic acids that have bound specifically to target molecules; (3) disassociating the nucleic acid-target complexes; (4) amplifying the nucleic acids disassociated from the nucleic acid-target complexes to yield a ligand-enriched mixture of nucleic acids; and (5) repeating the previous steps through as many cycles as desired or necessary to yield highly specific, high affinity aptamers to the target molecule.

A related process is the CE-SELEX (capillary electrophoresis-SELEX) process as described in J. Am. Chain. Soc. 2004, 126, 20-21. This technique uses electrophoresis to separate binding sequences from inactive ones. Selection occurs in free solution. Active sequences that bind the target undergo a mobility shift, similar to that seen in affinity capillary electrophoresis. Active sequences are separated from inactive sequences and collected as separate fractions.

A preferred method for identifying and isolating aptamers is the NECEEM (NonEquilibrium Capillary Electrophoresis of Equilibrium Mixtures) process as described in J. Am. Chem. Soc. 2002, 124, 13674-13675, Anal. Chem. 2003, 75, 1382-1386, Krylov, "NECEEM for Development, Characterization and Analytical Utilization of Aptamers," Lab Plus International, November 2005, and Krylov, "Nonequilibrium Capillary Electrophoresis of Equilibrium Mixtures (NECEEM): A Novel Method for Biological Screening," J. Biomol. Screen Online First, Jan. 17, 2006.

Briefly, this method starts with a naive DNA library (every sequence is statistically unique) that is mixed with the target protein and incubated to form an equilibrium mixture. DNA molecules with high affinity bind to the target protein, while those with low affinity do not bind. A plug of the equilibrium mixture is then introduced into a capillary, and a high voltage is applied. The equilibrium fraction of DNA-target is separated from the equilibrium fraction of DNA by gel-free capillary electrophoresis under non-equilibrium conditions. Under these conditions, the mobility of the target is higher than that of DNA, and the mobility of the target-DNA complex is typically intermediate between that of the DNA and the target. In the electric field, the zones are thus separated, and equilibrium between the three components is no longer maintained. The DNA-target complex starts disassociating, which results in "smears" of DNA and target between three peaks. Due to the high efficiency of separation, reattachment of disassociated DNA and target is negligible.

The components reach the end of the capillary in the following order: (1) the equilibrium part of free target; (2) free target formed by disassociation of DNA-target during NECEEM; (3) the remains of intact DNA-target; (4) free DNA formed from the disassociation of DNA-target during NECEEM; and (5) the equilibrium part of free DNA. A fraction is collected from the output of the capillary in a time window. The widest aptamer collection window includes DNA-target complexes and DNA disassociated from DNA-target complexes during NECEEM.

The preferred targets are polypeptides (peptides and proteins) on the sperm cells that are sex-specific or otherwise allow identification or separation of the sperm based on sex selection or other desired characteristics. Examples of such polypeptides are disclosed in U.S. Pat. Nos. 4,191,749; 4,448,767; 5,021,244; 6,153,373; and 6,489,092 and in U.S. Patent Application Publication 2003/0162238 A1. For example, the published patent application discloses an isolated sex-chromosome-specific protein characterized as follows: (a) X chromosome specific, (h) associated with the cell membrane of bovine sperm cells, and (e) having a molecular weight on SDS-PAGE of about 32 kDa.

Once suitable aptamers are selected, they may be produced and reproduced by many techniques well known to those of ordinary skill in the art, including enzymatic techniques or through chemical synthesis. Additional chemical groups may be added through known chemical techniques. Such groups include fluorescein or biotin and other groups that create a detectable signal. In addition, modified nucleotides may be used to protect the aptamers from degradation by nucleases. Such modified nucleotides include 2'-0-methyl and 2'-fluro derivatives.

In some embodiments, the aptamers selected and/or produced as described above will be used in an assay for separating populations of sperm cells based on whether they carry the X or Y chromosome, an abnormal number of sex chromosomes, or other desired sperm cell characteristics. In a preferred embodiment, the method of separating mammalian sperm cells comprises the steps of: 1) contacting the mammalian sperm cells with the aptamer of the invention and 2) separating the sperm cells into two or more populations based on the ability of the sperm cells to bind to the aptamer. In one embodiment, the method comprises the further step of separating the sperm cells hound to the aptamer from the aptamer and recovering the separated sperm cells. In another embodiment, the sperm cells that are not bound to the aptamer are recovered.

In an alternative embodiment, more than one type of aptamer maybe used. Thus, two or more aptamers of the invention may be used in the separation method and these aptamers may contain consensus sequences that bind to the same target molecule. Aptamers produced by the present method are useful for binding to target molecules and more specifically those target molecules on sperm cells, both X sperm cells and Y sperm cells.

This method produces sperm cell populations selected and separated based upon certain desired characteristics of the cells. Separated populations may be bound or unbound to the aptamer. If the desired population is bound to the aptamer, preferably the sperm cells are separated from the aptamer molecules. Preferably, the sperm cells are cattle sperm cells. In one preferred embodiment, the sperm cells contain a Y chromosome. In an alternative preferred embodiment, the sperm cells contain only the X chromosome.

In a further embodiment, the invention provides a method for producing an aptamer or nucleic acid sequence that permits separation of X sperm cells from Y sperm cells. This prepared aptamer is contacted with a mixed population of X and Y sperm cells, and the aptamer binds preferentially to the X sperm cells and these bound aptamer-X sperm cell complexes are separated from the original mixed sperm cell population leaving a Y containing rich sperm cell population. The bound aptamer-X containing sperm cell complex can be treated to release the X containing sperm cells so that they can be isolated as a population of cells.

An assay for separating sperm cells by use of aptamers could be used, for example, as follows. Commercially available, microscopically small magnetic beads are coated with an appropriate aptamer of the invention, such as X sperm specific aptamers. These beads will be placed in a suspension of the sperm-cells in an appropriate receptacle, such as a glass dish. Because the sex-chromosome-specific proteins are present on the cell surface, accessible from the cell surface or inside the cell, the X sperm cells will then bind to the X sperm specific/preferential aptamer on the beads, while the Y sperm cells will not or will bind less preferentially. The beads are then pulled to the side of the dish using a magnet. Sperm cells having the Y chromosome are then recovered. Other types of beads that can be used to capture and recover the aptamers may also be used. Additional techniques using magnetic beads coated with substances that bind to sperm cells are disclosed in U.S. Patent Application Publication Nos. 2003/0068654 A1, 2004/0142384 A1, and 2005/0114915 A1.

In another example, agglutination of sperm cells may be used. In such an approach, live, unsorted sperm may be suspended in a serum free, in vitro culture medium and exposed to either Y or X sperm cell specific/preferential aptamers. Following treatment, the medium is filtered in a glass wool filter, and sperm in the filtrate is used to perform in vitro fertilization.

In another example, the aptamers against X or Y sperm cell specific surface proteins or proteins accessible from the cell surface or inside the cell may bind to and inactivate X or Y sperm cells respectively, and may prevent them from fertilizing an ovum. The sperm cells not bound by the aptamers may remain viable and active for fertilizing ova. Thus, the invention provides a method to produce a semen sample enriched in active X or Y sperm cells and thus capable of increasing the probability that offspring will be of a desired sex or have a gene for a sex-chromosome linked trait.

In another example, a native sperm preparation may be exposed to a first aptamer that binds, for example, Y specific molecules. The exposed sperm may be suspended together with a conjugate of a second aptamer that binds exclusively to the first aptamer and an immunoabsorbent substrate in a protein-free diluent to form a conjugate/sperm preparation whereby the Y sperm are bound to the substrate. The Y sperm may then be recovered from the substrate by specific binding of the substrate.

The methods described herein provide the means to separate sperm on factors of quality and desirability, including sperm cell motility, functionality, stimulation, and preservation, which can affect fertility rates, insemination rates, fertilization rates, offspring health, and offspring desirability for various species of mammals, including, but not limited to, humans, horse, cattle, swine, cats, dogs, buffalo, oxen, and elk.

The methods for separating sperm on the basis of desired characteristics described herein minimize damage to the sperm by mechanical handling so that the sperm have improved viability. The methods are non-invasive, do not require chemical binding to cellular internal structures, involve minimal manipulation, and are inexpensive. There are minimal requirements for equipment or instrumentation and they are readily carried out by a person skilled in the art.

The aptamers prepared by the present method and methods of the present invention may also be used to evaluate other characteristics of the sperm. For example, they may be used to determine sperm quality, determine male fertility, identify healthy sperm, or identify abnormal or damaged sperm.

The separated sperm cells of the invention are preferably used for artificial insemination of a mammal. Preferably, the mammal is a bovine mammal. The method for artificial insemination comprises administering the sperm to the mammal using techniques known to those skilled in the art.

The invention farther comprises a kit for artificial insemination of a mammal. The kit contains at least the separated spoon cell population of the invention and optionally other components or devices to administer the sperm cell population to the mammal. Preferably, the kit contains the individual sperm cell sample in a tube for insertion into the vagina of the female animal. Such sample tube is known in the art as a "straw".

Alternatively, the separated sperm of the invention maybe used for in vitro fertilization of a mammal. Preferably, the mammal is a human being.

EXAMPLES

Sperm Aptamers Selection Method

A preferred method of selecting specific aptamers according to the present invention employs a method that utilizes several rounds of incubation of unsorted, sorted X and/or sorted Y sperm cells with a DNA library with a final step of collecting the solution with DNA binders and use it as a template for PCR and for strand separation on streptavadin beads. Applicants have determined that more than 6 rounds of sperm aptamer selection according to the present invention is optimal. Preferably 7 rounds, more preferably 8 rounds and even more preferably 9 rounds of selection are performed as outlined below. However, more than 9 rounds of selection can be performed if necessary to obtain aptamers that bind to the specific target molecule. It should be understood that the protocol described below can vary in temperature, volume, and other parameters that do not effect the outcome of the protocol but that will result in the production of specific aptamers that bind to target molecules. Such variations are known to persons skilled in the art.

Rounds 1-3 of Aptamer Selection
Preparation of Cells:
Thaw the sperm aliquot by placing the straw in 37° C. water for 1 min, and then keep the cells at room temperature (20-25° C.)(RT).

1. Take 1 straw of unsorted sperm cells (about 0.5 ml and $10^7$ cells).
2. Add 1 nil of the PVA (polyvinyl alcohol) containing semen buffer.
3. Spin the sperm cells for 12 min at 300×g at 17° C. in a 1.5 ml vial.
4. Remove the buffer and re-suspend cells in 1 ml of fresh PVA-semen buffer.
5. Spin the sperm cells for 12 min at 300×g at 17° C. in a 1.5 ml vials.
6. Resuspend the sperm cells in 300 μl of the fresh PVA-semen buffer and count the cells using chemocytometer. Dilute the cells to ~2×10$^6$ (40 000 cells per 20 μL) by adding 600 μL of buffer.
7. Anneal 50 μM of naive DNA library (custom ordered from Integrated DNA Technologies (IDT), Coralville, Iowa) with the following sequence: 5'-CTC CTC TGA CTG TAA CCA CG (SEQ ID NO: 1)-(40N)-GGC TTC TGG ACT ACC TAT GC (SEQ ID NO: 2)-3' dissolved in PBS (phosphate buffered saline buffer) with 2.5 mM MgCl$_2$ by heating to 94° C. for ~3 min, then cooling to RT.

8. Add 2 μL of 1 mM F-primer (forward primer custom ordered from IDT with the following sequence 5'-CTC CTC TGA CTG TAA CCA CG-3') (SEQ ID NO: 1) into the 40 μL aliquots of cells, to a final concentration of 50 μM. Fprimer is a first 20 nucleotides of the library. It is used in the selection as a background DNA. This sequence was chosen to decrease the likelihood that at least one of the constant regions of the library will not participate in the binding, and if removed will produce a shorter aptamer sequence but will not change the binding properties.
9. Add 4 μL, of 100 μM annealed library into the 20 μL, aliquot containing sperm cells with 50 μM F-primer.
10. Incubate for 1 hour at room temperature.
11 Add 200 μL of fresh PVA-semen buffer and spin for 12 min at 300×g at 17° C.
12. Remove the supernatant and re-dissolve the pellet in additional 200 μL of the PVA-semen buffer.
13. Spin for 12 min at 300×g at 17° C.
14. Remove the supernatant and re-dissolve the pellet in additional 200 μL, of the PVA-semen buffer.
15. Spin for 12 min at 300×g at 17° C.
16. Remove the supernatant and add 20 μL of the 10 mM Tris-HCl buffer, pH 7.5 and incubate cells at 95° C. for 5 min.
17. Spin down the cellular debris for 20 min at 20 000 rpm.
18. Collect the supernatant and use it as template for PCR using F primer and biotinylated R-primer (reverse primer custom ordered from IDT with the following sequence: 5'-biotin-GGC TTC TGG ACT ACC TAT GC-3') (SEQ ID NO: 2) and perform strand separation on streptavidin magnetic beads.

Completion of steps 1-18 above constitutes the completion of a single round. The supernatant from 18 is considered to be the Round 1 (R1) aptamer pool and is used directly or is amplified using known PCR techniques. For Round 2 (R2), the R1 aptamer pool is used in place of the naive DNA library in step 7 on a new sample of unsorted cells that are prepared according to steps 1-6. The supernatant or Round 2 (R2) aptamer pool from step 18 of the completion of Round 2 is then utilized directly or amplified using known PCR techniques and added in place of the DNA library in step 7 on a new sample of unsorted cells in Round 3 (R3). The supernatant from step 18 of Round 3 or the Round 3 (R3) aptamer pool is then used in step 7 of Round 4 described below.

Rounds 4-41 (Positive and Negative Selections with Sorted Cells)

Preparation of Cells:

Thaw the sperm aliquots (sorted X or sorted Y containing cells) by placing the straw in 37° C. water for 1 min, and then keep the cells at room temperature (20-25° C.).

Take 1 straw of sorted X and 1 straw of sorted Y
2. To each tube, then add 200 μl of fresh PVA semen buffer, and spin for 12 min at 300×g at 17° C., remove the supernatant leaving about 10 μl add 200 μl of fresh PVA-semen buffer and transfer all into the 200 μl PCR vial.
3. Spin the cells for 12 min at 300×g at 17° C. in a 0.2 ml PCR vials (smaller vials improves cell recovery) and remove the buffer leaving about 20 μl.
4. To each tube, add 60 μl of fresh PVA Semen buffer and split in 2 tubes by 30 μl.
5. Count the cells using chemocytometer. It should be around 2×10⁶ cells/ml (4×10⁴ cells per 20 μl).
6. About 1-2 min before addition of the R3 Aptamer pool (see step 18 of Round 3 above) to the cell suspension, add the F-primer to the final concentration of 50 μM (add 1 μl of 1 mM to 20 μL of cells).
7. For negative selection make the following mixtures:
    A. Y cells with 50 μM of F4 and 5 nM of X Apt pool from previous selection round (or R3 aptamer pool only if it is forth selection round).
    B. X cells with 50 μM of F4 and 5 nM of Y Apt pool from previous selection round (or R3 aptamer pool only if it is forth selection round). Incubate the mixtures at mom temperature or 1 hour and spin the cells down (300×g, 17° C. 12 min). Take the supernatant and use it in the positive selection. To each one of X and Y cells aliquots, add F-primer for a final concentration of 50 μM and equal amount of the supernatant from previous step.
    C. To X cells, add supernatant from fraction 1 to get 2.5 nM X aptamer pool and 50 μM F4.
    D. To Y cells, add supernatant from fraction 2 to get 2.5 nM Y aptamer pool and 50 μM F4.
8. Incubate the mixtures at room temperature for 1 hour.
9. Add 200 μL of fresh PVA-semen buffer and spin for 12 min at 300×g at 17° C.
10. Remove the supernatant and re-dissolve the pellet in additional 200 μL of the PVA-semen buffer.
11. Spin for 12 min at 300×g at 17° C.
12. Remove the supernatant and re-dissolve the pellet in additional 200 μL of the PVA-semen buffer.
13. Spin for 12 min at 300×g at 17° C.,
14. Remove the supernatant and add 20 μL of the buffer and incubate cells at 95° C. for 5 min.
15. Spin down the cellular debris for 20 min at 20 000 rpm.
16. Collect the supernatant or aptamer pool and use it as template for PCR and strand separation on streplavidin magnetic beads.

A round of the aptamer selection of Rounds 4-9 and higher rounds include steps 1-16 directly above. The Round 4 aptamer pool is then added to step 7 of the next round, Round 5, then the Round 5 aptamer pool is then added to step 7 of the next round, Round 6, then the Round 6 aptamer pool is then added to step 7 of the next round, Round 7, then the Round 7 aptamer pool is then added to step 7 of the next round, Round 8, then the Round 8 aptamer pool is then added to step 7 of the next round, Round 9, then the Round 9 aptamer pool is then added to step 7 of the next round, and any additional rounds can continue to be repeated accordingly.

The goal of these rounds of aptamer selection is to obtain a pool of aptamers that bind specifically to Y or X sperm cells. Therefore, at least Round 7 of the selection method should be run to obtain aptamers that specifically bind to the target molecule, more preferably at least Round 8 should be run and most preferably at least Round 9 or higher should be run to obtain a pool of aptamers that are specific for Y containing and X containing sperm.

Applicants submit that the above method can be utilized to prepare target specific aptamers of any type as long as the pool of cells that contain the target molecule that identifies the cell (unsorted or sorted) is substituted in the rounds of aptamer selection for the Y and X sperm cells both unsorted and sorted.

Cell Cytometry Analysis of Aptamers Produced in Aptamer Selection Method

The following method was performed to provide labeled pools of DNA and to provide a sufficient amount of DNA for analysis that could additionally save time and costs in the preparation. The known technique, asymmetric PCR, resulted in the production of one of the DNA strands. In order to determine if a pool of aptamers were good binders, labeled aptamers resulting from the asymmetric PCR technique were mixed with sperm cells and subjected to flow cell cytometry analysis. Naïve DNA library was used as a control.

Prepare the following mixture containing: 1 µM Alexa 647 (obtained from IDT as a custom primer) labelled forward primer (5'-Alexa 647-CTC CTC TGA CTG TAA CCA CG-3') (SEQ ID NO:1), 50 nM reverse primer (5'-GGC TTC TGG ACT ACC TAT GC-3') (SEQ ID NO: 2) 50 mM KCl, 10 mM Tris-HC (pH 8.6), 2.5 mM MgCl2, 200 µM of each deoxyribonucleotide triphosphate (dNTP), and 0.05 unit/µL Taq DNA polymerase.

There were 20 PCR cycles performed which includes a PCR cycle consisting of melting at 94° C. for 10 seconds, annealing at 56° C. for 10 seconds, and extension at 72° C. for 10 seconds. The first cycle has an extended melting step of 30 seconds. As a template, the purified single stranded aptamers pools after each selection round are used. After PCR is completed, the products are purified using the 30 kDA cut off DNA purification column (Microcon ultracel YM-30, from Millipore Bedford Mass., USA.) using standard procedure described in the manual and known to persons skilled in the art.

Preparation of cells: Thaw the sperm aliquot by placing the straw in 37° C. water for 1 min, and then keep the cells at room temperature (20-25° C.).

Take 1 or more straws of unsorted cells (about 0.5 ml and $10^7$ cells)
1. Add 1 ml of the PVA semen buffer.
2. Spin the cells for 12 min at 300×g at 17° C. in a 1.5 ml vial.
3. Remove the buffer and re-suspend cells in 1 ml of fresh PVA buffer.
4. Spin the cells for 12 min at 300×g at 17° C. in a 1.5 ml vial.
5. Re-suspend cells in 300 µl of the fresh PVA containing semen buffer and count the cells using haemocytometer.
6. Dilute cells to ~2×10$^6$ cells/ml (20 000-40 000 cells per 20 µL); and
7. 200 µl of cells+10 µl of 1 mM F4 primer then aliquot by 20 µl each.

In parallel:
1. Take 1 or more straws of sorted X and 1 or more straws of sorted Y cells.
2. Spin for 12 min at 300×g at 17° C., remove the supernatant leaving about 10 µL add 200 µl of fresh PVA Semen buffer and transfer all into the 200 µl PCR vial.
3. Spin the cells for 12 min at 300×g at 17° C. in a 0.2 ml PCR vials (smaller vials improves cell recovery) and remove the buffer leaving about 20 µl.
4. To each tube, then add 200 µl of fresh PVA. Semen buffer.
5. Count the cells using haemocytometer it should be around 2×10$^6$ cells/ml (4×10$^1$ cells per 20 µL).
6. Mix X cell mix with 1 mM F primer for a final concentration of 50 µM and make as many 20 µL aliquots as required for analysis.
7. Mix Y cell mix with 1 mM F primer for a final concentration of 50 µM and make as many 20 µL aliquots as required for analysis.
8. Mix unsorted cells with 1 mM F primer for a final concentration of 50 µM and make as many 20 µl aliquots as required for analysis.
9. Anneal the purified DNA libraries, and pools dissolved in PBS with 2.5 mM MgCl$_2$. (heat to 94° C. for ~3 min, then cool down at RT).
10. Add appropriate amounts of each aptamer pool from the rounds of aptamer selection described above that is to be tested into the 20 µL aliquot containing sperm cells with 50 µM F4 to a final concentration of ~10 nM: Make the following mixtures: unsorted, sorted X and sorted Y cells each with Naive DNA library and the pools from each selection round.
11. Incubate for 1 hour at room temperature.
12. Add 200 µL of fresh PVA-semen buffer and spin for 12 min at 300×g at 17° C.
13. Remove supernatant and add 200 µL of fresh PVA-buffer and transfer everything to the cell cytometry tube, and
14. Add the PI (propidium iodide, a nucleic acid stain and a dead cell marker, Sigma Aldrich) about 2-3 min before the analysis and additional 200 µL of the PVA-semen buffer.

FIG. 1 provides the analysis of the aptamers obtained by the present method in which 9 rounds of aptamer selection and analysis using flow cytometry was performed. Each population of live spermatozoa was represented by 8,000 to 9,000 cells. Live cells population were differentiated from dead cells by Propidium Iodide, a dead cell stain.

Comparing the binding of X sorted cells to the naïve library and to the X aptamer pool (FIG. 1, traces C and D, respectively), the results show that the X aptamer pool has about 10 times greater affinity to the X cells then the naïve library. This data shows that sperm cell specific aptamers were obtained from the library during the selection process. Then, the comparison of the binding affinities of X aptamer pool to X and Y sorted cells (FIG. 1, traces D and B, respectively) indicates that aptamer affinity to X cells is about 20 times greater then to Y cells. All the above data, together with the fact that the affinity of Y cells to the naïve DNA library, and to the X aptamer pool (FIG. 1, traces A and B, respectively) is relatively similar proves that the present method produces X cell specific aptamers, which can specifically bind to the X cells and has no, or very insignificant affinity to Y cells.

With regard to the binding of Y cells to the naïve DNA library and to the Y aptamer pool, data (not shown) shows that Y cells bind better to the Y aptamer pool than they do to the naïve DNA library which is indicative of Y specific aptamers.

After that six rounds of selection, the binding experiment was performed and the X pool of aptamers showed great binding affinity to the X cells and weak to no binding affinity to the Y cells (FIG. 2A). The Y pool of aptamers showed binding affinity to both the X and Y cells (FIG. 2B). The binding was observed using fluorescently labeled DNA and fluorescence confocal microscopy. The signal was measured using non-motile cells.

Generally, the present method provides aptamers that bind to target molecules that may or may not be on the surface of a cell but should be accessible from the surface of a cell, such as preferably a X or Y sperm cell containing X chromosomes and Y chromosomes, respectively. The cell cytometry analysis described herein provides a method to determine whether an aptamer pool obtained in the last step of a single round aptamer selection round as described herein contains one or more aptamers that bind to a target molecule. One should review the data and compare the binding of the aptamer pool with a sample containing the target molecule. This binding data should be compared with any binding of the same aptamer pool to the naïve DNA library, preferably the library from which the aptamer pools were first obtained as a negative control. Additionally, the aptamer pool binding also should be compared to a second or third sample that does not contain the target molecule. Results that show higher binding of the aptamer pool to the target molecule as compared to the binding to the naïve DNA library is considered as a positive preferential binding. Additionally, further rounds of selection as disclosed herein may increase the binding affinity of the aptamer pool. Additionally, if one wishes to separate two cell populations based on specific binding to one cell and not the other, such as with the separation of X and Y sperm cells, then in addition to comparing the binding of the aptamer pool to the naïve. DNA library, the aptamer pool binding also should be analyzed for its binding to the preferred target molecule as well as a sample containing the "non-target" molecule from which one wishes to separate the target molecule. In this latter instance, all of these comparisons should be analyzed to select aptamer pools that bind to a specific target molecules and do not bind or binds to a lesser degree or less preferentially to the cell or molecule from which one wants to separate the target molecule. Thus, using aptamers to separate different sperm cell populations requires analysis and comparison to different controls and negative controls.

Table 1 provides aptamers obtained from the aptamer pool after Round 9 according to the procedure provided above that bound preferentially to the X sperm cells and which did not bind or which bound less preferentially to the Y sperm cells than to the X sperm cells. The aptamers in Table 1 (SEQ ID NOS: 3-35) show portions of the nucleotides on the 5' end and the 3' end of each sequence that is underlined. These portions represent the constant regions of the aptamers that correspond to the forward primer CTC CTC TGA CTG TAA CCA CG (SEQ ID NO: 1) at the 5' end and the reverse primer, GGC TGG ACT ACC TAT GC (SEQ ID NO: 2) at the 3' end used to generate the aptamers from the naïve library, NP40. Each of these constant regions are 20 nucleotides in length. The aptamers of the present invention are intended to encompass the nucleotide length sequence of each of SEQ ID NOS: 3-35 or a portion thereof. In a further embodiment, an aptamer of the present invention comprises nucleotides 21-60 of SEQ ID NOS: 3-10 and 12-35 or portions thereof or nucleotides 21-43 of SEQ ID NO: 11 or portions thereof. For an aptamer (SEQ ID NOS: 3-35) or a portion of the recited sequence to be considered to be an aptamer within the meaning of the present invention, it must bind preferentially to a target molecule on an X or Y sperm cell at a higher affinity than any contaminating or control cells.

The DNA sequences in Table 1 represent selected sequences that were located in the Round 9 aptamer pool. Several of the sequences were present in the aptamer pool in multiple copies.

TABLE 1

SEQ ID NO: 3
CTCCTCTGACTGTAACCACGCACCGAATACAGACTGTAAAGACAGAAAGTTCATAAACGTGCATAGGTAG
TCCAGAAGCC

SEQ ID NO: 4
CTCCTCTGACTGTAACCACGTACGCTATTATTATTCAATAACGATAAGACTTATAATATAGCATAGGTAG
TCCAGAAGCC

SEQ ID NO: 5
CTCCTCTGACTGTAACCACGTATAATCATCGGGGTAAGTTGAGGCATTATCTACGCCATAGCATAGGTAG
TCCAGAAGCC

SEQ ID NO: 6
CTCCTCTGACTGTAACCACGATACCAATACGTAAATTCTATAAGGCATACATATTATACAAGCATAGGTA
GTCCAGAAGCC

SEQ ID NO: 7
CTCCTCTGACTGTAACCACGTCTGGAACATGATGCAGGTGTCTAACAGTATGAATACTTGGCATAGGTAG
TCCAGAAGCC

SEQ ID NO: 8
CTCCTCTGACTGTAACCACGCTGTCGACTACAGATCACTACTTTCGCTAAGGTACCTCAAGCATAGGTAG
TCCAGAAGCC

SEQ ID NO: 9
CTCCTCTGACTGTAACCACGTATAACGTTTTTCATCTATTTGTTTACTTAATACCTAATAGCATAGGTAG
TCCAGAAGCC

SEQ ID NO: 10
CTCCTCTGACTGTAACCACGATTGTATTAGTTAACGATACTTATTATTTGTAAGTTATTAGCATAGGTAG
TCCAGAAGCC

SEQ ID NO: 11
CTCCTCTGACTGTAACCACGAATAACATTACATATAGTTACTTGCATAGGTAGTCCAGAAGCC

SEQ ID NO: 12
CTCCTCTGACTGTAACCACGGTAAACATGATAATAATACTTCTCCTTTTGTAATGGATTTGCATAGGTAG
TCCAGAAGCC

SEQ ID NO: 13
CTCCTCTGACTGTAACCACGGGTACATATATCCCTATTAATTGACACATATATTTACTTAGCATAGGTAG
TCCAGAAGCC

TABLE 1-continued

SEQ ID NO: 14
CTCCTCTGACTGTAACCACGCATCATTTCGCTAATAGATAAAGTGTTCGTCGTCAGAGCAGCATAGGTAGTCCAGAAGCC

SEQ ID NO: 15
CTCCTCTGACTGTAACCACGATACATTTACGTAAATTCTATTAACATTTATATTCTACATGCATAGGTAGTCCAGAAGCC

SEQ ID NO: 16
CTCCTCTGACTGTAACCACGTAATATTAACTTTAAACTCCAATACTGTTATTTATCAAGTGCATAGGTAGTCCAGAAGCC

SEQ ID NO: 17
CTCCTCTGACTGTAACCACGGTATATCGACTTATTACAATGATAAGTATTATTAAACTTAGCATAGGTAGTCCAGAAGCC

SEQ ID NO: 18
CTCCTCTGACTGTAACCACGAAACATTACATGGAACTTGATCGTTTAGGATAATAAATGCGCATAGGTAGTCCAGAAGCC

SEQ ID NO: 19
CTCCTCTGACTGTAACCACGTGTACCACTTTCTGTTACGCTAATGGCACACTACACTTAAGCATAGGTAGTCCAGAAGCC

SEQ ID NO: 20
CTCCTCTGACTGTAACCACGTAACTTGGAATAATACTTCTTGTAAATTTTGCATAGGTAGTCCAGAAGCC

SEQ ID NO: 21
CTCCTCTGACTGTAACCACGTAAATATATGAGTTATTTATGAGTTCATTGAATTCTACTTGCATAGGTAGTCCAGAAGCC

SEQ ID NO: 22
CTCCTCTGACTGTAACCACGGAGTCAGCCTGATCTACCTTCAAAGGCCACTAGGCCTTGAGCATAGGTAGTCCAGAAGCC

SEQ ID NO: 23
CTCCTCTGACTGTAACCACGTATACTTACTTTACTAAAACTACTACTAAGTAAGTAAACAGCATAGGTAGTCCAGAAGCC

SEQ ID NO: 24
CTCCTCTGACTGTAAGCACGTATCACTTACATTTAAATCAATGTATATCAATATTTTAGTGCATAGGTAGTCCAGAAGCC

SEQ ID NO: 25
CTCCTCTGACTGTAACCACGTCAGGATAATGATCATAAGATATCTTTATGTATATACTATGCATAGGTAGTCCAGAAGCC

SEQ ID NO: 26
CTCCTCTGACTGTAACCACGCCAGTTCGTCATCAGATTCCATCTTTAGCTACTTACAACTGCATAGGTAGTCCAGAAGCC

SEQ ID NO: 27
CTCCTCTGACTGTAACCACGCAAAAGTCACTGGCCGTTCGAGTTATATGAGTAGGGAGAGGCATAGGTAGTCCAGAAGCC

SEQ ID NO: 28
CTCCTCTGACTGTAACCACGCCAGACCGGATCCCTGATGTATTTATTTTCGGAAGGTTGAGCATAGGTAGTCCAGAAGCC

SEQ ID NO: 29
CTCCTCTGACTGTAACCACGTAATGAGTGACGAAAGTGTCAGATGGAGCCTTCTACCTGTGCATAGGTAGTCCAGAAGCC

SEQ ID NO: 30
CTCCTCTGACTGTAACCACGCGATTAAAACCGGCAGTTATCTCTTAGCAAGCCTGATCCTGCATAGGTAGTCCAGAAGCC

SEQ ID NO: 31
CTCCTCTGACTGTAACCACGGGTTCAATGTAAGGGTTGGTGTGGTTGGACTAGCGCTCAGTGCATAGGTAGTCCAGAAGCC

SEQ ID NO: 32
CTCCTCTGACTGTAACCACGGCATATGTGAGCATCGAATAGCTGGCGACGAACCAGATTCGCATAGGTAGTCCAGAAGCC

SEQ ID NO: 33
CTCCTCTGACTGTAACCACGACGACAGTCATCCCTGACTCGGATCTTACATGTCGTTACAGCATAGGTAGTCCAGAAGCC

TABLE 1-continued

SEQ ID NO: 34
CTCCTCTGACTGTAACCACGTTAAATCTTATAGGATTCTAGTGTACAAATATATAACTTAGCATAGGTAG
TCCAGAAGCC

SEQ ID NO: 35
CTCCTCTGACTGTAACCACGCAAAAGTCACTGGCCGTTCGAGTTATATGAGTAGGGAGAGGCATAGGTAG
TCCAGAAGAT

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. The use of the words "a" or "an" herein to describe any aspect of the present invention is to be interpreted as indicating one or more.

Although this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for producing a nucleic acid sequence that permits separation of Y sperm cells from X sperm cells comprising the steps of:
   (a) obtaining a first sample of Y sperm cells and a second sample of X sperm cells;
   (b) producing a first group of nucleic acid sequences that bind to Y sperm cells in said first sample and a second group of nucleic acid sequences that bind to X sperm cells in said second sample; and
   (c) comparing said first and second groups of nucleic acid sequences to identify by process elimination at least one nucleic acid sequences that binds only to either the Y sperm cells or the X sperm cells.

\* \* \* \* \*